US011248095B2

(12) United States Patent
Berezin et al.

(10) Patent No.: US 11,248,095 B2
(45) Date of Patent: Feb. 15, 2022

(54) PHOTOINITIATORS FOR POLYOLEFINS

(71) Applicants: N3 COAT LTD., Caesarea (IL); MOBICHEM SCIENTIFIC ENGINEERING LTD, Jerusalem (IL)

(72) Inventors: Oleg Berezin, Maale Adumim (IL); Dan Rizkov, Beitar-Alite (IL); Boris Gorelik, Zur-Hadassa (IL)

(73) Assignee: N3 Coat Ltd. and Mobichem Scientific Engineering Ltd.

( * ) Notice: Subject to any disclaimer, the term of this patent is extended or adjusted under 35 U.S.C. 154(b) by 0 days.

(21) Appl. No.: 16/969,913

(22) PCT Filed: Feb. 14, 2019

(86) PCT No.: PCT/IL2019/050177
§ 371 (c)(1),
(2) Date: Aug. 13, 2020

(87) PCT Pub. No.: WO2019/159169
PCT Pub. Date: Aug. 22, 2019

(65) Prior Publication Data
US 2021/0115201 A1  Apr. 22, 2021

(30) Foreign Application Priority Data
Feb. 14, 2018 (IL) .......................................... 257535

(51) Int. Cl.
| C08F 2/46 | (2006.01) |
|---|---|
| C08F 2/50 | (2006.01) |
| C08G 61/04 | (2006.01) |
| C08J 3/28 | (2006.01) |
| C07C 49/84 | (2006.01) |
| C07C 59/13 | (2006.01) |
| C08J 3/24 | (2006.01) |
| C08K 5/06 | (2006.01) |

(52) U.S. Cl.
CPC ................. *C08J 3/28* (2013.01); *C07C 49/84* (2013.01); *C07C 59/13* (2013.01); *C08J 3/24* (2013.01); *C08K 5/06* (2013.01); *C08J 2323/06* (2013.01)

(58) Field of Classification Search
CPC ....... C07C 69/738; C07C 49/84; C07C 59/13; C08J 3/24; C08J 3/22; C08J 3/28; C08J 5/18; C08J 2323/08; C08J 2323/06; C08L 23/0815; C08L 23/06; C08L 2310/00; C08L 2203/16; C08L 2312/00; C08F 2/50; C08F 255/02; C08F 222/103; C08K 5/07; C08K 5/06; C08K 5/0025
USPC ........... 522/43, 33, 6, 71, 1, 189, 184; 520/1
See application file for complete search history.

(56) References Cited

U.S. PATENT DOCUMENTS

| 4,145,444 A | 3/1979 | Hamazaki et al. |
|---|---|---|
| 2002/0164480 A1* | 11/2002 | Martinotto ............. H01B 3/441 428/375 |
| 2009/0162767 A1 | 6/2009 | Wu |
| 2017/0114193 A1 | 4/2017 | Ericsson et al. |

FOREIGN PATENT DOCUMENTS

| AU | 2003239287 | | 9/2003 |
|---|---|---|---|
| CN | 101153062 | * | 4/2008 |
| CN | 101462936 A | | 6/2009 |
| EA | 002606 B1 | | 6/2002 |
| EP | 049085 B1 | | 5/1985 |
| EP | 837053 B1 | | 1/2003 |
| EP | 1972323 A2 | | 9/2008 |
| GB | 2119810 A | | 4/1983 |
| JP | 8175003 A2 | | 7/1996 |
| JP | 2009008755 A2 | | 1/2009 |
| WO | 1998028340 A1 | | 7/1998 |
| WO | 1998051759 A1 | | 11/1998 |
| WO | 2001008166 A1 | | 2/2001 |
| WO | 2001051440 A1 | | 7/2001 |
| WO | 2006042391 | | 4/2006 |
| WO | 2007048486 A1 | | 5/2007 |
| WO | 2007077258 A1 | | 7/2007 |
| WO | 2015162155 A1 | | 10/2015 |
| WO | 2016088549 A1 | | 6/2016 |
| WO | 2016088551 A1 | | 6/2016 |
| WO | 2017090725 A1 | | 6/2017 |

OTHER PUBLICATIONS

Xu et al, CN 101153062 Machine Translation, Apr. 2008 (Year: 2008).*
Zamotayev PV, Granchak VM, Litsov NI, Kachan AA, Influence of the Structure of Benzophenone Derivatives on the Efficiency of Crosslinking of Polyethylene Photo-Initiated by Them, Science Direct, Polymer Science U.S.S.R., vol. 27, Issue 10, 1985; pp. 2326-2334.
Wu Q, Qu B., Photoinitiating Characteristics of Benzophenone Derivatives as New Initiators in the Photocrosslinking of Polyethylene, Polymer Engineer and Science, Jul. 2001, vol. 41, No. 7, pp. 1220-1226.
Ruhlmann, D., Fouassier JP, Relations Structure—Proprietes Dans Les Photoamorceurs De Polymerisation, Eur. Polym. J. Vol. 27, No. 9, 1991, pp. 991-995.
Cheng, LL, Zhang Y, Shi WF., Photoinitiating Characteristics of Benzophenone Derivatives as Type II Macromolecular Photoinitiators Used for UV Curable Resins, Chem. Res. Chinese Universities, 2011, 27(1), pp. 145-149.
Wouters, M., Castell Muixi P., Wettability Aspects and the Improvement of Adhesion of UV Curable Powder Coatings on Polypropylene Substrates, Contact Angle, Wettability and Adhesion, Aug. 2008, vol. 5, 4 pages.
Merlin, A., Lougnot DJ, Fouassier JP., Laser Spectroscopy of Substituted Benzophenone Used as Photo-Initiators of Vinyl Polymerization , Aug. 1, 1980, Polymer Bulletin 2, pp. 847-853.
(Continued)

*Primary Examiner* — Jessica Whiteley
(74) *Attorney, Agent, or Firm* — McAndrews, Held & Malloy, Ltd.

(57) ABSTRACT

The technology disclosed herein concerns a family of alkoxybenzophenones for use as photoinitiators for cross-linking polyolefins.

18 Claims, No Drawings

(56) References Cited

OTHER PUBLICATIONS

Scully, Andrew D. et al., Transient Products in the Photoreduction of Benzophenone Derivatives in Poly (Ethylene-Vinyl Alcohol) Film, Science Direct, Journal of Photochemistry and Photobiology A: Chemistry, 197, 2008, pp. 132-140.
Yang-Jie Mao et al, Pd-Catalyzed Para-Selective C—H Difluoromethylation of Aryl Carbonyls, The Royal Society of Chemistry, Dec. 11, 2018, pp. 1-86.
Sharshira, Photocyclization Reactions. Part 5[1]. Synthesis of Dihydrobenzofuranols Using Photocyclization of 2-Alkoxybenzophenones and Ethyl 2-Benzoylphenoxyacetates, Journal of Heterocyclic Chemistry, 1996, 33(6), pp. 1797-1805.
Wenbo, Dehydrative Condensation of Carbonyls with Non-Acidic Methylenes Enabled by Light: Synthesis of Benzofurans, Chem. Commun., 2016, 52(89), pp. 13120-13123.
Database CA [online]: RN 750633-48-8, Entered STN: Sep. 24, 2004.
Papulov, Yu.G., Successes of Modern National Science, 2006, vol. 2, pp. 75-76 [English excerpt only].

\* cited by examiner

PHOTOINITIATORS FOR POLYOLEFINS

CROSS-REFERENCE TO RELATED APPLICATIONS

The present application is a National Phase Entry of PCT International Application No. PCT/IL2019/050177 which was filed on Feb. 14, 2019, which claims priority to Israel Application No. 257535, filed Feb. 14, 2018, all of which are hereby incorporated by reference in their entireties.

TECHNICAL FIELD

The invention generally concerns a novel family of photoinitiators.

BACKGROUND

With the rising importance of polyolefins in various fields of our lives, curing of polyolefins has become of greater importance. However, curing has thus far been achieved by ionizing radiation of high energy (electron beam or gamma-irradiation) which enabled cleavage of C—H bonds in the polyolefin molecule, yielding free radicals, and subsequent crosslinking into larger macro-molecules and finely, three dimensional network. While curing of polyolefins by irradiation of a lower energy, such as UV light, is also possible, available photoinitiators that are typically used for photocuring of acrylic monomers and oligomers cannot be used for photo-crosslinking of polyolefins due to substantial incompatibility with the polyolefins.

The successful photocuring of a polyethylene melt was realized in [1].

US Patent application US 2017/0114193 [2] Norrish-II photoinitiators of the benzophenone derivatives were used for photo-crosslinking of pipes made of polyethylene.

BACKGROUND ART

[1] EP 0490854
[2] US 2017/0114193
[3] JP8175003

GENERAL DESCRIPTION

The inventors of the present invention have developed a family of alkoxybenzophenones that may be used as photoinitiators for crosslinking polyolefins. The photoinitiators of the present invention exhibit high efficacy of photo-curing and high compatibility with the polyolefin or co-polymer to be crosslinked. The high solubility of the photoinitiators accounts for the observed interaction of exited states of photoirradiated benzophenone derivative (Norrish II mechanism of radical initiating) and polymer molecule on the molecular level, thereby substantially increasing transfer of energy from the photoinitiator to the polymer molecule, followed by formation of an alkyl radical by destruction of a C—H bond of the polyolefin or the co-polymer.

Thus, in a first aspect of the invention, there is provided an alkoxybenzophenone for use as a photoinitiator.

The invention further provides a photoinitiator formulation or composition comprising or consisting at least one alkoxybenzophenone, the formulation or composition being configured for use in a method of crosslinking at least one polyolefin.

The invention further contemplates use of at least one alkoxybenzophenone as a photoinitiator for use in a method of crosslinking at least one polyolefin.

The "alkoxybenzophenone" is at least one benzophenone substituted on one or both of its phenyl rings with one or more alkoxy groups. As known in the art, an "alkoxy" group is the group O-alkyl, wherein the alkyl may comprise between 1 and 20 carbon atoms. The alkyl group may be substituted or unsubstituted, linear or branched, or may be in the form of a substituted or unsubstituted carbocyclyl comprising 5 or 6 carbon atoms.

The alkoxy group may be substituted on the benzophenone skeleton at any position relative to the carbonyl group. The benzophenone may be substituted by one or more alkoxy groups, as defined. Where two or more alkoxy groups are present, they may be on the same phenyl ring or substituting both rings. The groups may be vicinal to each other or at any relative position. At least two alkoxy groups may be ortho-, meta- or para- to each other, or relative to the ipso carbon, or may be at any other relative position (relative to the carbonyl group).

In some embodiments, the alkoxy group is of the formula

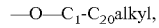

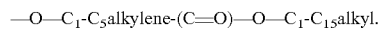

Each of the alkylene and alkyl groups is selected, independently from the other, from carbon chains or groups having 1, 2, 3, 4, 5, 6, 7, 8, 9, 10, 11, 12, 13, 14, 15, 16, 17, 18, 19 or 20 carbon atoms. Where the alkylene or alkyl group is limited by the number of carbon atoms, e.g., $C_1$-$C_5$alkylene or $C_1$-$C_5$alkyl, the number of carbon atoms in the carbon chain is within the lower limit and the upper limit indicated, inclusive, e.g., between 1 and 5 carbon atoms, inclusive. Thus, a group designated as $C_1$-$C_5$alkylene would comprise 1, 2, 3, 4, or 5 carbon atoms.

In some embodiments, the alkoxy group is selected from —O—$(CH_2)_n$—$CH_3$ and —O—$(CH_2)_n$—(C=O)—O—$(CH_2)_m$—$CH_3$, wherein each n and m, independently of the other, is an integer selected from 0 to 2, 0 to 3, 0 to 4, 0 to 5, 0 to 6, 0 to 7, 0 to 8, 0 to 9, 0 to 10, 0 to 11, 0 to 12, 0 to 13, 0 to 14, 0 to 15, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 2 to 4, 2 to 5, 2 to 6, 2 to 7, 2 to 8, 2 to 9, 2 to 10, 2 to 11, 2 to 12, 2 to 13, 2 to 14, 2 to 15, 3 to 5, 3 to 6, 3 to 7, 3 to 8, 3 to 9, 3 to 10, 3 to 11, 3 to 12, 3 to 13, 3 to 14, 3 to 15, 4 to 6, 4 to 7, 4 to 8, 4 to 9, 4 to 10, 4 to 11, 4 to 12, 4 to 13, 4 to 14, 4 to 15, 5 to 7, 5 to 8, 5 to 9, 5 to 10, 5 to 11, 5 to 12, 5 to 13, 5 to 14, 5 to 15, 6 to 8, 6 to 9, 6 to 10, 6 to 11, 6 to 12, 6 to 13, 6 to 14, 6 to 15, 7 to 9, 7 to 10, 7 to 11, 7 to 12, 7 to 13, 7 to 14, 7 to 15, 8 to 10, 8 to 11, 8 to 12, 8 to 13, 8 to 14, 8 to 15, 9 to 11, 9 to 12, 9 to 13, 9 to 14, 9 to 15, 10 to 12, 10 to 13, 10 to 14, 10 to 15, 11 to 13, 11 to 14, 11 to 15, 12 to 14, 12 to 15, 13 to 15, 14, 15, 14 to 20, 15 to 20, 16 to 20, 17 to 20, or 18 to 20.

In some embodiments, where integers n and m are recited, each n and m may be the same or different.

Where the alkoxy is —O—$(CH_2)_n$—$CH_3$, n may be an integer between 0 and 20, 0 and 15, 0 and 10, 0 and 3 or between 4 and 15.

In some embodiments, the benzophenone comprises one —O—$(CH_2)_n$—$CH_3$, wherein n is an integer between 0 and 15, 0 and 10, 0 and 3 or between 4 and 15.

In some embodiments, the benzophenone comprises two or more —O—$(CH_2)_n$—$CH_3$ groups, wherein n is an integer between 0 and 15, 0 and 10, 0 and 3 or between 4 and 15. The integer n may or may not be identical to both groups.

In some embodiments, n is between 1 and 15, or between 4 and 15, or between 5 and 15, or between 10 and 15. In some embodiments, n is 1, 3, 7, 9, 11 or 15.

In some embodiments, the alkoxy group is —O—$(CH_2)_n$—$CH_3$ group, wherein n zero.

In some embodiments, the benzophenone is free of —O—$(CH_2)_n$—$CH_3$ groups.

Where the alkoxy is —O—$(CH_2)_n$—(C=O)—O—$(CH_2)_m$—$CH_3$, wherein each n and m, independently of the other, may be an integer between 0 and 3 or between 4 and 15.

In some embodiments, n is between 1 and 15, or between 4 and 15, or between 5 and 15, or between 10 and 15. In some embodiments, n is 1, 3, 7, 9, 11 or 15.

In some embodiments, n is 0, 1, 2 or 3.
In some embodiments, n is 0
In some embodiments, n is 1.

In some embodiments, m is between 1 and 15, or between 4 and 15, or between 5 and 15, or between 10 and 15. In some embodiments, m is 1, 3, 7, 9, 11 or 15.

In some embodiments, m is 0, 1, 2 or 3.
In some embodiments, m is 0
In some embodiments, m is 1.

In some embodiments, the benzophenone comprises one —O—$CH_2$—(C=O)—O—$(CH_2)_m$—$CH_3$, wherein m is an integer between 0 and 3 or between 4 and 15, as selected hereinabove. In some embodiments, the benzophenone comprises two or more —O—$CH_2$—(C=O)—O—$(CH_2)_m$—$CH_3$ groups, wherein m is an integer between 0 and 3 or between 4 and 15, as selected hereinabove.

In some embodiments, the benzophenone is free of —O—$CH_2$—(C=O)—O—$(CH_2)_m$—$CH_3$ or —O—$(CH_2)_n$—(C=O)—O—$(CH_2)_m$—$CH_3$.

In some embodiments, the alkoxy group is —O—$CH_2$—(C=O)—O—$(CH_2)_m$—$CH_3$ group, wherein m is zero.

In some embodiments, the alkoxybenzophenone is of the general Formula (I).

The invention further provides a benzophenone Norish II photoinitiator, the benzophenone having one or two carbon moieties ortho to the carbonyl group, and at least one hydrogen atom at a position γ to the carbonyl group, wherein the carbon moieties are ether moieties.

The invention further provides an alkoxybenzophenone of the general Formula

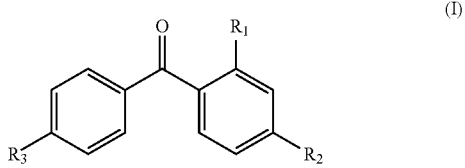

(I)

wherein at least one of $R_1$, $R_2$, and $R_3$, independently of the other, is an alkoxy group, e.g., a $C_1$-$C_{20}$alkoxy group, at least another of said $R_1$, $R_2$, and $R_3$ is optionally an alkyl group, e.g., a $C_1$-$C_{20}$alkyl group, wherein at least two of said $R_1$, $R_2$, and $R_3$ are different from hydrogen (and are therefore selected from the alkoxy and/or alkyl groups).

As used herein, the group $C_1$-$C_{20}$alkoxy is a group selected from —O—$C_1$-$C_{20}$alkyl, —O—$C_1$-$C_{10}$alkylene-(C=O)—O—$C_1$-$C_{10}$alkyl, and —O—$C_1$-$C_5$alkylene-(C=O)—O—$C_1$-$C_{15}$alkyl. In other words, the group "$C_1$-$C_{20}$alkoxy" is interchangeable herein with —O—$C_1$-$C_{20}$alkyl, —O—$C_1$-$C_{10}$alkylene-(C=O)—O—$C_1$-$C_{10}$alkyl, or —O—$C_1$-$C_5$alkylene-(C=O)—O—$C_1$-$C_{15}$alkyl. As indicated above, for each of the alkylene and alkyl groups, independently from the other, the number of carbon atoms may be 1, 2, 3, 4, 5, 6, 7, 8, 9, 10, 11, 12, 13, 14, 15, 16, 17, 18, 19 or 20. Where the alkylene or alkyl group is limited by the number of carbon atoms, e.g., $C_1$-$C_5$alkylene or $C_1$-$C_5$alkyl, the number of carbon atoms in the carbon chain is within the lower limit and the upper limit indicated, inclusive, e.g., between 1 and 5 carbon atoms, inclusive. Thus, a group designated as $C_1$-$C_5$alkylene would comprise 1, 2, 3, 4, or 5 carbon atoms.

As used herein, the group $C_1$-$C_{20}$alkyl is an alkyl group containing between 1 and 20 carbon atoms, 1 and 20 atoms inclusive, which may be linear or branched or may be substituted. In some embodiments, the number of carbon atoms in the alkyl chain may be selected 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 2 to 4, 2 to 5, 2 to 6, 2 to 7, 2 to 8, 2 to 9, 2 to 10, 2 to 11, 2 to 12, 2 to 13, 2 to 14, 2 to 15, 3 to 5, 3 to 6, 3 to 7, 3 to 8, 3 to 9, 3 to 10, 3 to 11, 3 to 12, 3 to 13, 3 to 14, 3 to 15, 4 to 6, 4 to 7, 4 to 8, 4 to 9, 4 to 10, 4 to 11, 4 to 12, 4 to 13, 4 to 14, 4 to 15, 5 to 7, 5 to 8, 5 to 9, 5 to 10, 5 to 11, 5 to 12, 5 to 13, 5 to 14, 5 to 15, 6 to 8, 6 to 9, 6 to 10, 6 to 11, 6 to 12, 6 to 13, 6 to 14, 6 to 15, 7 to 9, 7 to 10, 7 to 11, 7 to 12, 7 to 13, 7 to 14, 7 to 15, 8 to 10, 8 to 11, 8 to 12, 8 to 13, 8 to 14, 8 to 15, 9 to 11, 9 to 12, 9 to 13, 9 to 14, 9 to 15, 10 to 12, 10 to 13, 10 to 14, 10 to 15, 11 to 13, 11 to 14, 11 to 15, 12 to 14, 12 to 15, 13 to 15, 14, 15, 14 to 20, 15 to 20, 16 to 20, 17 to 20, or 18 to 20.

In some embodiments, $R_1$ is —O—$(CH_2)_n$—$CH_3$ or —O—$(CH_2)_n$—(C=O)—O—$(CH_2)_m$—$CH_3$, wherein each of n and m, independently of the other, is an integer as defined herein. In some embodiments, each of n and m, independently of the other is between 0 and 3.

In some embodiments, $R_2$ is —H, —$(CH_2)_n$—$CH_3$ or —O—$(CH_2)_n$—$CH_3$, wherein n is an integer as defined hereinabove. In some embodiments, n is between 4 and 15.

In some embodiments, $R_3$ is —H, —$(CH_2)_n$—$CH_3$, —O—$(CH_2)_n$—$CH_3$ or —O—(C=O)—$(CH_2)_m$—$CH_3$, wherein each of n and m, independently of the other, is an integer as defined hereinabove. In some embodiments, each of n and m, independently of the other, is between 4 and 15.

In some embodiments, in a compound of formula (I):
$R_1$ is —O—$(CH_2)_n$—$CH_3$ or —O—$(CH_2)_n$—(C=O)—O—$(CH_2)_m$—$CH_3$, wherein for each variant, independently, each of n and m, independently of the other, is between 0 and 3 (being 0, 1, 2 or 3);

$R_2$ is —H, —$(CH_2)_n$—$CH_3$ or —O—$(CH_2)_n$—$CH_3$, wherein for each variant, independently, each n is an integer between 4 and 15 (being 4, 5, 6, 7, 8, 9, 10, 11, 12, 13, 14 or 15); and $R_3$ is —H, —$(CH_2)_n$—$CH_3$, —O—$(CH_2)_n$—$CH_3$ or —O—(C=O)—$(CH_2)_m$—$CH_3$, wherein for each variant, independently, each of n and m, independently of the other, is an integer between 4 and 15 (being 4, 5, 6, 7, 8, 9, 10, 11, 12, 13, 14 or 15).

In some embodiments, $R_1$ is —O—$(CH_2)_n$—$CH_3$ or —O—$CH_2$—(C=O)—O—$(CH_2)_m$—$CH_3$, wherein each of n and m, independently of the other, is an integer between 0 and 3 and $R_2$ is —H, —$(CH_2)_n$—$CH_3$ or —O—$(CH_2)_n$—$CH_3$, wherein n is an integer between 4 and 15.

In some embodiments, $R_1$ is —O—$(CH_2)_n$—$CH_3$ or —O—$CH_2$—(C=O)—O—$(CH_2)_m$—$CH_3$, wherein each of n and m, independently of the other, is an integer between 0 and 3 and $R_3$ is —H, —$(CH_2)_n$—$CH_3$, —O—$(CH_2)_n$—$CH_3$ or —O—(C=O)—(CH$_2$)$_m$—CH$_3$, wherein each of n and m, independently of the other, is an integer between 4 and 15.

In some embodiments, R$_2$ is —H, —(CH$_2$)$_n$—CH$_3$ or —O—(CH$_2$)$_n$—CH$_3$, wherein n is an integer between 4 and 15 and R$_3$ is —H, —(CH$_2$)$_n$—CH$_3$, —O—(CH$_2$)$_n$—CH$_3$ or —O—(C=O)—(CH$_2$)$_m$—CH$_3$, wherein each of n and m, independently of the other, is an integer between 4 and 15.

In some embodiments, in compounds of the invention, R$_1$ is —O—CH$_2$—CH$_3$.

In some embodiments, in compounds of the invention, R$_1$ is —O—CH$_2$—(C=O)—O—CH$_2$—CH$_3$.

In some embodiments, in compounds of the invention, R$_2$ is —O—(CH$_2$)$_7$—CH$_3$.

In some embodiments, in compounds of the invention, R$_2$ is —(CH$_2$)$_7$—CH$_3$.

In some embodiments, a compound is a compound of general Formula (I), wherein R$_1$ is —O—CH$_3$, R$_2$ is —O—(CH$_2$)$_7$—CH$_3$ and R$_3$ is H.

In some embodiments, a compound is a compound of general Formula (I), wherein R$_1$ is —O—CH$_3$, R$_2$ is —O—(CH$_2$)$_9$—CH$_3$ and R$_3$ is H.

In some embodiments, a compound is a compound of general Formula (I), wherein R$_1$ is —O—CH$_3$, R$_2$ is —O—(CH$_2$)$_{11}$—CH$_3$ and R$_3$ is H.

In some embodiments, a compound is a compound of general Formula (I), wherein R$_1$ is —O—CH$_2$—CH$_3$, R$_2$ is —O—(CH$_2$)$_7$—CH$_3$ and R$_3$ is H.

In some embodiments, a compound is a compound of general Formula (I), wherein R$_1$ is —O—CH$_2$—CH$_3$, R$_2$ is —O—(CH$_2$)$_9$—CH$_3$ and R$_3$ is H.

In some embodiments, a compound is a compound of general Formula (I), wherein R$_1$ is —O—CH$_2$—CH$_3$, R$_2$ is —O—(CH$_2$)$_{11}$—CH$_3$ and R$_3$ is H.

In some embodiments, a compound is a compound of general Formula (I), wherein R$_1$ is —O—CH$_2$—(C=O)—O—CH$_3$, R$_2$ is —O—(CH$_2$)$_7$—CH$_3$ and R$_3$ is H.

In some embodiments, a compound is a compound of general Formula (I), wherein R$_1$ is —O—CH$_2$—(C=O)—O—CH$_3$, R$_2$ is —O—(CH$_2$)$_9$—CH$_3$ and R$_3$ is H.

In some embodiments, a compound is a compound of general Formula (I), wherein R$_1$ is —O—CH$_2$—(C=O)—O—CH$_3$, R$_2$ is —O—(CH$_2$)$_{11}$—CH$_3$ and R$_3$ is H.

In some embodiments, a compound is a compound of general Formula (I), wherein R$_1$ is —O—CH$_2$—(C=O)—O—CH$_2$—CH$_3$, R$_2$ is —O—(CH$_2$)$_7$—CH$_3$ and R$_3$ is H.

In some embodiments, a compound is a compound of general Formula (I), wherein R$_1$ is —O—CH$_2$—(C=O)—O—CH$_2$—CH$_3$, R$_2$ is —O—(CH$_2$)$_9$—CH$_3$ and R$_3$ is H.

In some embodiments, a compound is a compound of general Formula (I), wherein R$_1$ is —O—CH$_2$—(C=O)—O—CH$_2$—CH$_3$, R$_2$ is —O—(CH$_2$)$_{11}$—CH$_3$ and R$_3$ is H.

In some embodiments, a compound is a compound of general Formula (I), wherein R$_1$ is —O—CH$_3$, R$_2$ is —O—(CH$_2$)$_7$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_3$, R$_2$ is —O—(CH$_2$)$_9$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_3$, R$_2$ is —O—(CH$_2$)$_{11}$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—CH$_3$, R$_2$ is —O—(CH$_2$)$_7$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—CH$_3$, R$_2$ is —O—(CH$_2$)$_9$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—CH$_3$, R$_2$ is —O—(CH$_2$)$_{11}$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—(C=O)—O—CH$_3$, R$_2$ is —O—(CH$_2$)$_7$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—(C=O)—O—CH$_3$, R$_2$ is —O—(CH$_2$)$_9$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—(C=O)—O—CH$_3$, R$_2$ is —O—(CH$_2$)$_{11}$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—(C=O)—O—CH$_2$—CH$_3$, R$_2$ is —O—(CH$_2$)$_7$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—(C=O)—O—CH$_2$—CH$_3$, R$_2$ is —O—(CH$_2$)$_9$—CH$_3$ and R$_3$ is —(CH$_2$)$_n$—CH$_3$, —O—(CH$_2$)$_n$—CH$_3$ or —O—(C=O)—(CH$_2$)$_m$—CH$_3$, wherein for each variant, independently, each of n and m, independently of the other, is an integer between 4 and 15 (being 4, 5, 6, 7, 8, 9, 10, 11, 12, 13, 14 or 15).

In some embodiments, a compound is a compound of general Formula (I), wherein R$_1$ is —O—CH$_2$—(C=O)—O—CH$_2$—CH$_3$, R$_2$ is —O—(CH$_2$)$_{11}$—CH$_3$ and R$_3$ is —(CH$_2$)$_n$—CH$_3$, —O—(CH$_2$)$_n$—CH$_3$ or —O—(C=O)—

$(CH_2)_m$—$CH_3$, wherein for each variant, independently, each of n and m, independently of the other, is an integer between 4 and 15 (being 4, 5, 6, 7, 8, 9, 10, 11, 12, 13, 14 or 15).

The invention further provides a compound selected from:
- a compound of general Formula (I), wherein $R_1$ is —O—$CH_3$, $R_2$ is —O—$(CH_2)_7$—$CH_3$ and $R_3$ is H;
- a compound of general Formula (I), wherein $R_1$ is —O—$CH_3$, $R_2$ is —O—$(CH_2)_9$—$CH_3$ and $R_3$ is H;
- a compound of general Formula (I), wherein $R_1$ is —O—$CH_3$, $R_2$ is —O—$(CH_2)_{11}$—$CH_3$ and $R_3$ is H;
- a compound of general Formula (I), wherein $R_1$ is —O—$CH_2$—$CH_3$, $R_2$ is —O—$(CH_2)_7$—$CH_3$ and $R_3$ is H;
- a compound of general Formula (I), wherein $R_1$ is —O—$CH_2$—$CH_3$, $R_2$ is —O—$(CH_2)_9$—$CH_3$ and $R_3$ is H;
- a compound of general Formula (I), wherein $R_1$ is —O—$CH_2$—$CH_3$, $R_2$ is —O—$(CH_2)_{11}$—$CH_3$ and $R_3$ is H;
- a compound of general Formula (I), wherein $R_1$ is —O—$CH_2$—(C=O)—O—$CH_3$, $R_2$ is —O—$(CH_2)_7$—$CH_3$ and $R_3$ is H;
- a compound of general Formula (I), wherein $R_1$ is —O—$CH_2$—(C=O)—O—$CH_3$, $R_2$ is —O—$(CH_2)_9$—$CH_3$ and $R_3$ is H;
- a compound of general Formula (I), wherein $R_1$ is —O—$CH_2$—(C=O)—O—$CH_3$, $R_2$ is —O—$(CH_2)_{11}$—$CH_3$ and $R_3$ is H;
- a compound of general Formula (I), wherein $R_1$ is —O—$CH_2$—(C=O)—O—$CH_2$—$CH_3$, $R_2$ is —O—$(CH_2)_7$—$CH_3$ and $R_3$ is H;
- a compound of general Formula (I), wherein $R_1$ is —O—$CH_2$—(C=O)—O—$CH_2$—$CH_3$, $R_2$ is —O—$(CH_2)_9$—$CH_3$ and $R_3$ is H; and
- a compound of general Formula (I), wherein $R_1$ is —O—$CH_2$—(C=O)—O—$CH_2$—$CH_3$, $R_2$ is —O—$(CH_2)_{11}$—$CH_3$ and $R_3$ is H.

Each of the compounds of the invention may be separately selected and used. Thus, compounds of the invention may be
- a compound of general Formula (I), wherein $R_1$ is —O—$CH_3$, $R_2$ is —O—$(CH_2)_7$—$CH_3$ and $R_3$ is H; or
- a compound of general Formula (I), wherein $R_1$ is —O—$CH_3$, $R_2$ is —O—$(CH_2)_9$—$CH_3$ and $R_3$ is H; or
- a compound of general Formula (I), wherein $R_1$ is —O—$CH_3$, $R_2$ is —O—$(CH_2)_{11}$—$CH_3$ and $R_3$ is H; or
- a compound of general Formula (I), wherein $R_1$ is —O—$CH_2$—$CH_3$, $R_2$ is —O—$(CH_2)_7$—$CH_3$ and $R_3$ is H; or
- a compound of general Formula (I), wherein $R_1$ is —O—$CH_2$—$CH_3$, $R_2$ is —O—$(CH_2)_9$—$CH_3$ and $R_3$ is H; or
- a compound of general Formula (I), wherein $R_1$ is —O—$CH_2$—$CH_3$, $R_2$ is —O—$(CH_2)_{11}$—$CH_3$ and $R_3$ is H; or
- a compound of general Formula (I), wherein $R_1$ is —O—$CH_2$—(C=O)—O—$CH_3$, $R_2$ is —O—$(CH_2)_7$—$CH_3$ and $R_3$ is H; or
- a compound of general Formula (I), wherein $R_1$ is —O—$CH_2$—(C=O)—O—$CH_3$, $R_2$ is —O—$(CH_2)_9$—$CH_3$ and $R_3$ is H; or
- a compound of general Formula (I), wherein $R_1$ is —O—$CH_2$—(C=O)—O—$CH_3$, $R_2$ is —O—$(CH_2)_{11}$—$CH_3$ and $R_3$ is H; or
- a compound of general Formula (I), wherein $R_1$ is —O—$CH_2$—(C=O)—O—$CH_2$—$CH_3$, $R_2$ is —O—$(CH_2)_7$—$CH_3$ and $R_3$ is H; or
- a compound of general Formula (I), wherein $R_1$ is —O—$CH_2$—(C=O)—O—$CH_2$—$CH_3$, $R_2$ is —O—$(CH_2)_9$—$CH_3$ and $R_3$ is H; or
- a compound of general Formula (I), wherein $R_1$ is —O—$CH_2$—(C=O)—O—$CH_2$—$CH_3$, $R_2$ is —O—$(CH_2)_{11}$—$CH_3$ and $R_3$ is H.

In some embodiments, the compound is a compound of general Formula (I), wherein $R_1$ is —O—$CH_3$, $R_2$ is —O—$(CH_2)_7$—$CH_3$ and $R_3$ is H.

In some embodiments, the compound is a compound of general Formula (I), wherein $R_1$ is —O—$CH_3$, $R_2$ is —O—$(CH_2)_9$—$CH_3$ and $R_3$ is H.

In some embodiments, the compound is a compound of general Formula (I), wherein $R_1$ is —O—$CH_3$, $R_2$ is —O—$(CH_2)_{11}$—$CH_3$ and $R_3$ is H.

In some embodiments, the compound is a compound of general Formula (I), wherein $R_1$ is —O—$CH_2$—$CH_3$, $R_2$ is —O—$(CH_2)_7$—$CH_3$ and $R_3$ is H.

In some embodiments, the compound is a compound of general Formula (I), wherein $R_1$ is —O—$CH_2$—$CH_3$, $R_2$ is —O—$(CH_2)_9$—$CH_3$ and $R_3$ is H.

In some embodiments, the compound is a compound of general Formula (I), wherein $R_1$ is —O—$CH_2$—$CH_3$, $R_2$ is —O—$(CH_2)_{11}$—$CH_3$ and $R_3$ is H.

In some embodiments, the compound is a compound of general Formula (I), wherein $R_1$ is —O—$CH_2$—(C=O)—O—$CH_3$, $R_2$ is —O—$(CH_2)_7$—$CH_3$ and $R_3$ is H.

In some embodiments, the compound is a compound of general Formula (I), wherein $R_1$ is —O—$CH_2$—(C=O)—O—$CH_3$, $R_2$ is —O—$(CH_2)_9$—$CH_3$ and $R_3$ is H.

In some embodiments, the compound is a compound of general Formula (I), wherein $R_1$ is —O—$CH_2$—(C=O)—O—$CH_3$, $R_2$ is —O—$(CH_2)_{11}$—$CH_3$ and $R_3$ is H.

In some embodiments, the compound is a compound of general Formula (I), wherein $R_1$ is —O—$CH_2$—(C=O)—O—$CH_2$—$CH_3$, $R_2$ is —O—$(CH_2)_7$—$CH_3$ and $R_3$ is H.

In some embodiments, the compound is a compound of general Formula (I), wherein $R_1$ is —O—$CH_2$—(C=O)—O—$CH_2$—$CH_3$, $R_2$ is —O—$(CH_2)_9$—$CH_3$ and $R_3$ is H.

In some embodiments, the compound is a compound of general Formula (I), wherein $R_1$ is —O—$CH_2$—(C=O)—O—$CH_2$—$CH_3$, $R_2$ is —O—$(CH_2)_{11}$—$CH_3$ and $R_3$ is H.

In some embodiments, a compound of the invention or a compound used according to the invention is at least one compounds recited in any of the Tables provided herein, excluding compounds of the art.

Compounds of the invention may be used as photoinitiators in crosslinking polyolefins. As known in the art, a "photoinitiator" is a compound that forms free radicals when activated, e.g. by exposure to light in the UV-C and UV-B region, or interaction with a co-initiator in a photochemical process. Photoinitiators of the invention are unique in their capability to photoinitiate crosslinking of or preparation of polyolefinic materials. The polyolefinic material is a single material, a combination of two or more material or any polymeric formulation that comprises, as one of polymeric materials, a polyolefinic material. The polyolefin (or polyolefinic material) generally refers to homopolymers, or copolymers having a methylene linkage between monomer units which may be formed by use of a photoinitiator of the invention. Examples of polyolefins includes polymers such as polyethylene and ethylene copolymers with a copolymer such as ethylene-alpha olefin copolymers, polyethylene (PE), polypropylene, low density polyethylene (LDPE), linear low-density polyethylene (LLDPE), very low-density polyethylene (VLDPE), ultra-low-density polyethylene (ULDPE), medium-density polyethylene (MDPE), high-density polyethylene (HDPE), ultra-high-density polyethylene (UHDPE), ethylene/propylene copolymers, polypropylene (PP), propylene/ethylene copolymer, ethylene and ethylene, alcohol copolymer (EVOH), ethylene and propylene copolymer, polyisoprene, polybutylene, polybutene, poly-3-methylbutene-1, poly-4-methylpentene-1, or copolymers of ethylene with one or more alpha-olefins such as butene-1, hexene-1 or octene-1.

The photoinitiators of the invention may be used as such or in combination with one or more additives. In some embodiments, the photoinitiator is comprised in a composition that further comprises at least one additive. The at least one additive may be selected from antioxidants, cross-linkers, UV absorbers, light stabilizers, flame retardants, optical brighteners, antistatic agents, anti-hydrolyzing agents, carriers, diluents, pigments or coloring agents, and others.

A photoinitiator formulation according to the invention may be a solid formulation or a liquid formulation, or may be tailored based on, inert alia, the polyolefin used, the photoinitiator chosen for the specific purpose, presence of other additives, and other considerations. Therefore, depending e.g., on the purposed use of a photoinitiator according to the invention, the photoinitiator may be formulated. In some embodiments, the photoinitiator is preformulated as a master batch or as a kit comprising a predetermined quantity in solid, liquid or formulated form.

The invention further provides a method of crosslinking at least one polyolefin, the method comprising contacting at least one UV-crosslinkable polyolefin material or a composition comprising same with at least one photoinitiator of the invention and irradiating said polyolefin under conditions causing crosslinking.

Where the method utilizes a composition of the at least one UV-crosslinkable polyolefin, the composition may further comprise one or more additives such as compatibilisers, fillers (organic or inorganic), nanofillers, glass and ceramic microspheres, glass fibres, flame retardants, antioxidants, stabilizers, processing aids, foaming agents, peroxides, pigments and coloring agents and others.

The invention further provides a method for manufacturing an article of a UV-crosslinkable polyolefin, the method comprising forming, by any means known in the art (e.g., extrusion, moulding or by other means), said article and subjecting the article to UV radiation while being formed; the article comprising an amount of at least one photoinitiator of the invention.

The crosslinking of the at least one polyolefin takes place under UV irradiation. The irradiation method may involve irradiation, namely exposure of the polymer or composite made thereof to a UV radiation source. Irradiation of the polyolefin mixed with the photoinitiator generates free-radicals on the polymer chains which then covalently combine to effect crosslinking of the polymer. A major advantage of using photoinitiators of the invention resides in their high efficacy due to their ability to cross-link polyolefins in atmospheric conditions, e.g., when exposed to air, even in case of very thin films (less than 10 microns), requiring low concentrations of, e.g., less than 0.5%, without needing the presence of promoters such as acrylic monomers and oligomers.

The UV radiation source may be one or more UV lamp or an assembly of UV lamps capable of emitting radiation in the wavelength range between 100 and 500 nm. Generally speaking, the UV source used is selected to have an emission spectrum matching the absorption spectrum of the photoinitiator selected.

The crosslinking may be achieved as a separate process step in a process for making an article of polyolefine. The process may involve melting of the polyolefin, processing the polyolefin and forming an article therefrom. The photoinitiator used according to the invention may be added at any stage of the process, such that the crosslinking step may be introduced on-line with any of the processing steps.

Notwithstanding the processing steps or sequence, the polyolefin-containing may be prepared by mixing or blending the polyolefin and the photoinitiator, as well as any additional additive, prior to melt the composition. In some cases, the components of the composition may be melt blended (by, a continuous single-screw or twin-screw extrusion compounder, kneader, or internal batch mixer) to form the homogenous composition that is eventually crosslinked.

Batch compositions of the polyolefin or polyolefin blend and the photoinitiator may be performed into pellets and stored for subsequent use. Articles formed according to methods of the invention may be formed from such pelleted master batches or by combining the components immediately prior to carrying out the process of the invention.

The amount of the at least one photoinitiator may vary to provide an amount that is effective to accelerate crosslinking of the polyolefin. In some embodiments, the photoinitiator may be added in an amount ranging from 0.1 to 10% (by weight). In some embodiments, the amount is between 0.1 and 0.5%, or between 0.1 and 5%, or between 0.5 and 10%, or between 0.5 and 5% (by weight).

DETAILED DESCRIPTION OF EMBODIMENTS

High efficacy photo-curing can be provided only in case photoinitiator and polymer possess high compatibility, namely both polyolefin or co-polymer and photoinitiator of the invention have to have similar values of Hansen solubility parameters. More specifically, the vector differences in polar, dispersive and hydrogen bonds components of Hansen solubility parameters ($\delta_p$, $\delta_d$, $\delta_h$) are to be less than 6.0 $(J/cm^3)^{1/2}$.

High solubility of photoinitiators of the invention accounts for interaction of exited state of photoirradiated benzophenone derivative (Norrish II mechanism of radical initialization) and a polymer molecule on the molecular level, to increase substantially transfer of energy from the photoinitiator to the polymer molecule, followed by formation of an alkyl radical by destruction of a C—H bond of the polyolefin or the co-polymer.

In the Table 1 below, the Hansen solubility parameters for pure benzophenone photoinitiators and polyethylene are presented.

TABLE 1

Solubility parameters of benzophenone and polyethylene

| Solubility parameters $(J/cm^3)^{1/2}$ | $\delta_d$ | $\delta_p$ | $\delta_h$ |
|---|---|---|---|
| Polyethylene | 17.6 | 0 | 0 |
| Benzophenone | 19.5 | 7.2 | 5.1 |

The vector difference of the solubility parameters is 9 $(J/cm^3)^{1/2}$. This is more than the solubility limit of 6 $(J/cm^3)^{1/2}$. As a result, benzophenone bloom out of polyethylene without any substantive photocuring after irradiation of a polyethylene composition containing an amount of the pure benzophenone.

Photoinitiators of the invention possesses satisfactory solubility on polyethylene starting.

In Table 2, data on solubility parameters of benzophenone derivative according to general Formula (II) the invention are presented.

TABLE 2

Solubility parameters of benzophenone derivatives according to the invention.

| Photoinitiator type | Solubility parameters $(J/cm^3)^{1/2}$ | $\delta_d$ | $\delta_p$ | $\delta_h$ |
|---|---|---|---|---|
| 1* | $R_1 =$ —O—$CH_2$—$CH_3$, $R_2$: —O—$(CH_2)_7$—$CH_3$, $R_3 = H$ | 18.8 | 4.5 | 3.0 |
| 2** | $R_1 =$ —O—$CH_2$—CO—O—$CH_2$—$CH_3$, $R_2 =$ —O—$(CH_2)_7$—$CH_3$ | 19.0 | 4.8 | 3.2 |

*Photoinitiator of type 1 can be easily synthesized using well known UV-absorber Chimassorb 81 (CAS# 1843-05-6) with $BrCH_2$—$CH_3$.
**Photoinitiator of type 2 can be obtained from the same UV-absorber by reaction with ethyl ester of chloro-acetic acid.

For the first benzophenone derivative in Table 2, the vector difference with solubility parameter of polyethylene is 5.5 $(J/cm^3)^{1/2}$ and for the second derivative that difference is 5.9 $(J/cm^3)^{1/2}$. That means that both benzophenone derivatives have a solubility parameter which is smaller than 6.0 $(J/cm^3)^{1/2}$ and as such both exhibit solubility in polyethylene.

Introduction of either photoinitiators of Table 2 in LDPE up to 5% w/w did not lead to any appreciable blooming effect which could have resulted from migration of the photoinitiator out of polymer matrix.

In the below Examples, the efficiency of photo-induced cross-linking of photoinitiators according to the invention is presented with different polyolefins.

Photoinitiators different from those of the invention, yet having a comparable compatibility with polyolefins were used as comparative examples. These were 4-octyloxybenzophenone, CAS #1843-05-6, 1- and 4-hydroxybenzophenone laurate, CAS #35820-92-9 listed in Table 2 above.

It is well known that direct introduction of additives into polymers, as powders or liquids, leads to inhomogeneous distribution followed by non-even cross-linking Thus, before final mixing with polyolefins, master batches of particular photoinitiators were prepared. Concentration of the photoinitiator in the master batches was 10% w/w. Master batches were produced by a twin screw extruder with construction of screws providing very homogeneous distribution of the photoinitiators in the master batch. Adding master batches into virgin polyethylene following this procedure, and photo-irradiating the composition, resulted in reproducible results.

Two types of experiments utilizing photoinitiators of the invention are presented in the examples below:

Cross-linking films made of LDPE in a single bubble extrusion process in order to improve tensile properties of films (e.g. for packaging), while keeping UV-treated polymer in a form capable of melt welding;

Cross-linking of LLDPE primary tube of oriented films made by a double bubble technology, in order to increase tensile properties of the melt during orientation of first bubble by inflation (stretching).

In the case of the film of the first type above, a LDPE film was UV-irradiated off line. Irradiation of the film was conducted from both sides.

In case of the oriented film, production UV-sources were placed on both sides of a primary tube before orientation. UV-treatment was performed on line.

For both types of films, efficiency of cross-linking was tested by measuring creep of film (1.0 inch width) at 135° C. with a loading weight of between 50 g and 57 g.

1.0 mm, 2.0 mm and 3.0 mm thick slabs of different polyolefins (LDPE, HDPE) were prepared by a method of melt pressing to simulate cables insulating coatings or pipes. Master batches of cross-linking promoters [e.g., trimethylol propane tri-methacrylate (TMPTMA) and Triallylisocyanurate (TAIC)] were added as master batches containing between 5 and 25% of the cross-linking promoter. Efficiency of used UV-initiators was tested by measurement of gel fraction in the irradiated polymer by extraction of sol fraction by boiled Xylene.

Slabs were irradiated with UV-light from a UV-lamp and conveyer.

Power of the UV-lamps used was 1.0 kW. Appropriate equipment was used to measure exposure dose in $J/cm^2$.

Table 3 presents data on exposure dose needed to cross-link samples to get creep time of 15 sec for acquiring desired tensile properties.

TABLE 3

Exposure dose in $J/cm^2$ to obtain creep time for irradiated LDPE films 30 micron thick containing photoinitiators according to Formula (II) and for comparative photoinitiators.

| Number | Sample name | Concentration of photo-initiator, % | Exposure Dose*, $J/cm^2$ |
|---|---|---|---|
| 1 | According to Formula (I), $R_1 =$ —O—$CH_2$—$CH_3$, $R_2 =$ O—$(CH_2)_7$—$CH_3$, $R_3 = H$ | 0.3 | 3.5 |
| 2 | According to Formula (I), $R_1 =$ —O—$CH_2$—CO—O—$CH_2$—$CH_3$, $R_2 =$ —O—$(CH_2)_7$—$CH_3$, $R_3 = H$ | 0.25 | 3.0 |
| 3 | 4-octyloxybenzophenone, CAS#1843-05-6 (comparative) | 0.35 | 4.6 |
| 4 | 4-hydroxybenzophenone laurate, CAS#35820-92-9, (Comparative) | 0.35 | 4.8 |

*Exposure dose of UV-irradiation to get 15 sec creep time, 135 C., 57 g load

As may be noted from Table 3, photoinitiators of Formula (I) and (II) proved to be substantially effective in photo-cross-linking LDPE, as compared to the comparative photoinitiators. For the comparative photoinitiators, the concentrations must be higher in order to achieve crosslinking to achieve a 15 sec creep time In Table 4, data are presented on the exposure dose needed to obtain 15 sec creep time for oriented LLDPE films, 20 micron thick in case of on line UV-irradiation of primary tube of 0.4 mm thick.

TABLE 4

Exposure dose in $J/cm^2$ to obtain creep time 15 sec for LLDPE irradiated films containing photo-initiator according to Formula (II) and for comparative photo-initiators. UV-treatment was applied on line on primary tube before orientation to obtain 20 micron thick film.

| Number | Sample name | Concentration of photo-initiator, % | Exposure Dose*, $J/cm^2$ |
|---|---|---|---|
| 1 | According to Formula (I), $R_1 = —O—CH_2—CH_3$, $R_2 = O—(CH_2)_{11}—CH_3$, $R_3 = H$ | 0.35 | 4.0 |
| 2 | According to Formula (I), $R_1 = —O—CH_2—CO—O—CH_2—CH_3$, $R_2 = —O—(CH_2)_7—CH_3$, $R_3 = H$ | 0.35 | 3.8 |
| 3 | 4-octyloxybenzophenone, CAS#1843-05-6 (Comparative) | 0.35 | 5.0 |
| 4 | 4-hydroxybenzophenone laurate, CAS#35820-92-9, (Comparative) | 0.4 | 5.5 |

*Exposure dose of UV-irradiation to get 15 sec creep time, 135° C., 57 g load.

It is clear from Table 4, that photo-curing based on photoinitiators of Formula (I) and (II) proved to be more effective as compared to compositions based on comparative photoinitiators.

In Table 5 data is presented on exposure dose needed to achieve 65% gel fraction in samples made of different polyethylenes and of different thickness.

TABLE 5

Exposure doses ($J/cm^2$) needed to obtain 65% gel fraction in different samples of polyethylenes of different thickness.

| Number | Sample name | Thickness (mm) | Conc. of PI, % | Promoter Concentration (TMPTMA), % | Expos. Dose*, $J/cm^2$ |
|---|---|---|---|---|---|
| 1 | According to Formula (I), $R_1 = —O—CH_2—CH_3$, $R_2 = O—(CH_2)_{11}—CH_3$, $R_3 = H$ | 1 | 1.0 | 1.0 | 45 |
| 2 | According to Formula (I), $R_1 = —O—CH_2—CH_3$, $R_2 = O—(CH_2)_{11}—CH_3$, $R_3 = H$ | 2 | 1.0 | 1.0 | 102 |
| 3 | According to Formula (I), $R_1 = —O—CH_2—CO—O—CH_2—CH_3$, $R_2 = —O—(CH_2)_7—CH_3$, $R_3 = H$ | 2 | 1.0 | 1.0 | 45 |
| 4 | According to Formula (I), $R_1 = —O—CH_2—CO—O—CH_2—CH_3$, $R_2 = —O—(CH_2)_7—CH_3$, $R_3 = H$ | 3 | 1.0 | 1.0 | 100 |
| 5 | 4-octyloxybenzophenone CAS#1843-05-6 (Comparative) | 1.0 | 1.2 | 1.2 | 60 |
| 6 | 4-octyloxybenzophenone CAS#1843-05-6 (Comparative) | 2.0 | 1.3 | 1.3 | 145 |
| 7 | 4-hydroxybenzophenone laurate, CAS#35820-92-9, (Comparative) | 1.0 | 1.0 | 1.0 | 78 |
| 8 | 4-hydroxybenzophenone laurate, CAS#35820-92-9, (Comparative) | 3.0 | 1.3 | 1.3 | 168 |

Data in Table 5 shows that compositions based on photoinitiators of Formula (I) and (II) are substantially more effective than those used in the comparative samples.

The invention claimed is:

1. A photoinitiator for use in a method of crosslinking at least one polyolefin, wherein the photoinitiator is an alkoxybenzophenone of the general Formula (I):

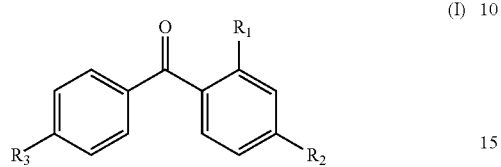

wherein
(i) $R_1$ is $-O-(CH_2)_n-(C=O)-O-(CH_2)_m-CH_3$, wherein for each variant, independently, each of n and m, independently of the other, is between 0 and 3;
$R_2$ is H, $-(CH_2)_n-CH_3$ or $-O-(CH_2)_n-CH_3$, wherein for each variant, independently, each n is an integer between 4 and 15; and
$R_3$ is H, $-(CH_2)_n-CH_3$, $-O-(CH_2)_n-CH_3$ or $-O-(C=O)-(CH_2)_m-CH_3$, wherein for each variant, independently, each of n and m, independently of the other, is an integer between 4 and 15; or
(ii) $R_1$ is $-O-(CH_2)_n-CH_3$ wherein n is between 1 and 3, or $-O-(CH_2)_n(C=O)-O-(CH_2)_m-CH_3$, wherein of n and m, independently of the other, is between 0 and 3;
$R_2$ is $-H$, $-(CH_2)_n-CH_3$ or $-O-(CH_2)_n-CH_3$, wherein for each variant, independently, each n is an integer between 4 and 15; and
$R_3$ is $-H$, $-(CH_2)_n-CH_3$, $-O-(CH_2)_n-CH_3$ or $-O-(C=O)-(CH_2)_m-CH_3$, wherein for each variant, independently, each of n and m, independently of the other, is an integer between 4 and 15; or
(iii) $R_1$ is $-O-(CH_2)_nCH_3$ or $-O-(CH_2)_n-(C=O)-O-(CH_2)_m-CH_3$, wherein for each variant, independently, each of n and m, independently of the other, is between 0 and 3;
$R_2$ is $-H$, $-(CH_2)_n-CH_3$ or $-O-(CH_2)_n-CH_3$, wherein for each variant, independently, each n is an integer between 4 and 15; and
$R_3$ is $-H$, $-(CH_2)_n-CH_3$, $-O-(CH_2)_n-CH_3$ or $-O-(C=O)-(CH_2)_m-CH_3$, wherein for each variant, independently, each of n and m, independently of the other, is an integer between 4 and 15;
provided that when $R_1$ is $-O-CH_3$, at least one of $R_2$ and $R_3$ is different from H.

2. The photoinitiator according to claim 1, wherein $R_1$ is $-O-CH_2-CH_3$.

3. The photoinitiator according to claim 1, wherein $R_1$ is $-O-CH_2-(C=O)-O-CH_2-CH_3$.

4. The photoinitiator according to claim 1, wherein $R_1$ is $-O-CH_3$, $R_2$ is $-O-(CH_2)_7-CH_3$ and $R_3$ is H; or wherein $R_1$ is $-O-CH_3$, $R_2$ is $-O-(CH_2)_9-CH_3$ and $R_3$ is H; or wherein $R_1$ is $-O-CH_3$, $R_2$ is $-O-(CH_2)_{11}-CH_3$ and $R_3$ is H; or wherein $R_1$ is $-O-CH_2-CH_3$, $R_2$ is $-O-(CH_2)_7-CH_3$ and $R_3$ is H; or wherein $R_1$ is $-O-CH_2-CH_3$, $R_2$ is $-O-(CH_2)_9-CH_3$ and $R_3$ is H; or wherein $R_1$ is $-O-CH_2-CH_3$, $R_2$ is $-O-(CH_2)_{11}-CH_3$ and $R_3$ is H; or wherein $R_1$ is $-O-CH_2-(C=O)-O-CH_3$, $R_2$ is $-O-(CH_2)_7-CH_3$ and $R_3$ is H; wherein $R_1$ is $-O-CH_2-(C=O)-O-CH_3$, $R_2$ is $-O-(CH_2)_9-CH_3$ and $R_3$ is H; or wherein $R_1$ is $-O-CH_2-(C=O)-O-CH_3$, $R_2$ is $-O-(CH_2)_{11}-CH_3$ and $R_3$ is H; or wherein $R_1$ is $-O-CH_2-(C=O)-O-CH_2-CH_3$, $R_2$ is $-O-(CH_2)_7-CH_3$ and $R_3$ is H; or wherein $R_1$ is $-O-CH_2-(C=O)-O-CH_2-CH_3$, $R_2$ is $-O-(CH_2)_9-CH_3$ and $R_3$ is H; or wherein $R_1$ is $-O-CH_2-(C=O)-O-CH_2-CH_3$, $R_2$ is $-O-(CH_2)_{11}-CH_3$ and $R_3$ is H.

5. A compound of Formula (I):

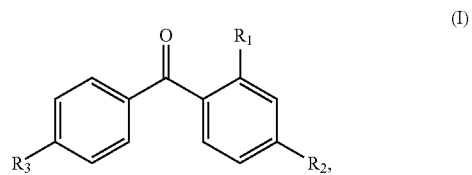

the compound being selected from:
a compound wherein $R_1$ is $-O-CH_3$, $R_2$ is $-O-(CH_2)_7-CH_3$ and $R_3$ is H;
a compound wherein $R_1$ is $-O-CH_3$, $R_2$ is $-O-(CH_2)_9-CH_3$ and $R_3$ is H;
a compound wherein $R_1$ is $-O-CH_3$, $R_2$ is $-O-(CH_2)_{11}-CH_3$ and $R_3$ is H;
a compound wherein $R_1$ is $-O-CH_2-CH_3$, $R_2$ is $-O-(CH_2)_7-CH_3$ and $R_3$ is H;
a compound wherein $R_1$ is $-O-CH_2-CH_3$, $R_2$ is $-O-(CH_2)_9-CH_3$ and $R_3$ is H;
a compound wherein $R_1$ is $-O-CH_2-CH_3$, $R_2$ is $-O-(CH_2)_{11}-CH_3$ and $R_3$ is H;
a compound wherein $R_1$ is $-O-CH_2-(C=O)-O-CH_3$, $R_2$ is $-O-(CH_2)_7-CH_3$ and $R_3$ is H;
a compound wherein $R_1$ is $-O-CH_2-(C=O)-O-CH_3$, $R_2$ is $-O-(CH_2)_9-CH_3$ and $R_3$ is H;
a compound wherein $R_1$ is $-O-CH_2-(C=O)-O-CH_3$, $R_2$ is $-O-(CH_2)_{11}-CH_3$ and $R_3$ is H;
a compound wherein $R_1$ is $-O-CH_2-(C=O)-O-CH_2-CH_3$, $R_2$ is $-O-(CH_2)_7-CH_3$ and $R_3$ is H;
a compound wherein $R_1$ is $-O-CH_2-(C=O)-O-CH_2-CH_3$, $R_2$ is $-O-(CH_2)_9-CH_3$ and $R_3$ is H; and
a compound wherein $R_1$ is $-O-CH_2-(C=O)-O-CH_2-CH_3$, $R_2$ is $-O-(CH_2)_{11}-CH_3$ and $R_3$ is H.

6. The compound according to claim 5, being:
a compound wherein $R_1$ is $-O-CH_3$, $R_2$ is $-O-(CH_2)_7-CH_3$ and $R_3$ is H; or
a compound wherein $R_1$ is $-O-CH_3$, $R_2$ is $-O-(CH_2)_9-CH_3$ and $R_3$ is H; or
a compound wherein $R_1$ is $-O-CH_3$, $R_2$ is $-O-(CH_2)_{11}-CH_3$ and $R_3$ is H; or
a compound wherein $R_1$ is $-O-CH_2-CH_3$, $R_2$ is $-O-(CH_2)_7-CH_3$ and $R_3$ is H; or
a compound wherein $R_1$ is $-O-CH_2-CH_3$, $R_2$ is $-O-(CH_2)_9-CH_3$ and $R_3$ is H; or
a compound wherein $R_1$ is $-O-CH_2-CH_3$, $R_2$ is $-O-(CH_2)_{11}-CH_3$ and $R_3$ is H; or
a compound wherein $R_1$ is $-O-CH_2-(C=O)-O-CH_3$, $R_2$ is $-O-(CH_2)_7-CH_3$ and $R_3$ is H; or
a compound wherein $R_1$ is $-O-CH_2-(C=O)-O-CH_3$, $R_2$ is $-O-(CH_2)_9-CH_3$ and $R_3$ is H; or
a compound wherein $R_1$ is $-O-CH_2-(C=O)-O-CH_3$, $R_2$ is $-O-(CH_2)_{11}-CH_3$ and $R_3$ is H; or
a compound wherein $R_1$ is $-O-CH_2-(C=O)-O-CH_2-CH_3$, $R_2$ is $-O-(CH_2)_7-CH_3$ and $R_3$ is H; or a compound wherein R₁ is —O—CH₂—(C=O)—O—CH₂—CH₃, R₂ is —O—(CH₂)₉—CH₃ and R₃ is H; or
a compound wherein R₁ is —O—CH₂—(C=O)—O—CH₂—CH₃, R₂ is —O—(CH₂)₁₁—CH₃ and R₃ is H.

7. The compound according to claim 5, wherein the compound is for use as a photoinitiator.

8. A photoinitiator being a compound according to claim 5.

9. A composition comprising at least one compound according claim 5, and optionally at least one polyolefin.

10. The composition according to claim 9, further comprising at least one promoter.

11. The composition according to claim 9, comprising at least one olefin and at least one promoter.

12. The composition according to claim 10, wherein the at least one promoter is selected from trimethylol propane tri-methacrylate (TMPTMA) and triallylisocyanurate (TAIC).

13. The composition according to claim 10, comprising between 0.5 and 5 wt % promoter.

14. The composition according to claim 9, comprising at least one photoinitiator at a concentration of between 0.01 and 10 wt %.

15. The composition according to claim 14, wherein the at least one photoinitiator is at a concentration of between 0.05 and 5 wt %.

16. A master batch comprising at least one photoinitiator according to claim 5, and optionally at least one promoter.

17. A method of crosslinking at least one polyolefin, the method comprising treating, under irradiation, said at least one polyolefin with an amount of a photoinitiator according to claim 5.

18. The method according to claim 17, wherein the polyolefin is selected from polyethylene and ethylene copolymers, polyethylene (PE), polypropylene, low density polyethylene (LDPE), linear low-density polyethylene (LLDPE), very low-density polyethylene (VLDPE), ultra-low-density polyethylene (ULDPE), medium-density polyethylene (MDPE), high-density polyethylene (HDPE), ultra-high-density polyethylene (UHDPE), ethylene/propylene copolymers, polypropylene (PP), propylene/ethylene copolymer, ethylene and ethylene, alcohol copolymer (EVOH), ethylene and propylene copolymer, polyisoprene, polybutylene, polybutene, poly-3-methylbutene-1, poly-4-methylpentene-1, or copolymers of ethylene with one or more alpha-olefins.

\* \* \* \* \*